United States Patent [19]

Roussel

[11] Patent Number: 4,499,897

[45] Date of Patent: Feb. 19, 1985

[54] OPTICAL HEAD OF AN INSTALLATION FOR OBSERVATION AND TREATMENT OF THE EYE BY LASER RADIATION

[75] Inventor: Philippe Roussel, NL-Wassenaar, Netherlands

[73] Assignee: Lasag AG, Switzerland

[21] Appl. No.: 472,934

[22] Filed: Mar. 7, 1983

[30] Foreign Application Priority Data

Mar. 11, 1982 [CH] Switzerland ............ 1495/82

[51] Int. Cl.³ .............. A61B 17/36; A61N 3/00; G02B 27/14

[52] U.S. Cl. .................. 128/303.1; 350/172; 350/438; 219/121 LU; 219/121 LS; 219/121 LQ; 128/395

[58] Field of Search .............. 128/303.1, 395; 219/121 LP, 121 LQ, 121 LR, 121 LS, 121 LT, 121 LU, 121 LV, 121 LW, 121 LX; 351/217; 372/14-15; 350/438, 171-172

[56] References Cited

U.S. PATENT DOCUMENTS

| | | | |
|---|---|---|---|
| 2,838,601 | 6/1958 | Cavanagh | 350/171 |
| 2,960,612 | 11/1960 | Koulicovitch | 350/171 |
| 3,704,061 | 11/1972 | Travis | 350/171 |
| 3,710,798 | 1/1973 | Bredemeier | 128/395 |
| 4,081,807 | 3/1978 | Urano et al. | 350/171 |
| 4,289,378 | 9/1981 | Remy et al. | 219/121 LS |
| 4,391,519 | 7/1983 | Kuwabara et al. | 219/121 LU |

Primary Examiner—C. Fred Rosenbaum
Assistant Examiner—Gene B. Kartchner
Attorney, Agent, or Firm—Peter L. Berger

[57] ABSTRACT

The optical head of an installation for observation and treatment by a laser beam of an eye comprises a mirror disposed between an observing microscope and a focusing lens for reflecting towards the latter a treatment and a marking laser radiation beam forming a visible envelope of the treatment beam. That mirror has an outer portion intersecting the marking beam only and an inner portion intersecting the treatment beam only. That inner portion has a reflection coefficient which is maximum for the wavelength of the treatment beam and minimum for the wavelength of the marking beam, so that the latter only is allowed to reach the observing microscope after reflection on the zone of the eye to be treated.

9 Claims, 2 Drawing Figures

OPTICAL HEAD OF AN INSTALLATION FOR OBSERVATION AND TREATMENT OF THE EYE BY LASER RADIATION

BACKGROUND AND SUMMARY OF THE INVENTION

This invention concerns installations for observation and treatment of the eye by laser radiation and it relates, in particular, to the optical head of such an installation.

A number of eye diseases, like, for example, different types of glaucomas or cataracts, or the disorders resulting from the formation of membranes or filaments of different origins in the eye, can at present be treated by the application of high-density laser radiation in certain regions of the anterior of posterior chamber of the eye.

For that purpose, generally complex ophthalmological treatment installations are used, which combine a stationary laser power generator to produce the laser treatment beam and a moving optical head that can be brought close to the patient's eye and making it possible, notably, to train the treatment beam on the zone to be treated.

An installation of that type is described, for example, in the European patent application published under No. 0 030 210 in the applicant's name. The laser power generator it uses is an Nd-YAG laser that can deliver on Q-Switch mode very short and very high-intensity pulses. The optical head of the installation contains in turn a device for illumination and observation of the zone of the eye to be treated and a marking laser beam generator.

The marking beam is produced, for example, by an He-Ne laser and is formed then by visible radiation. Its function is to materialize the focusing spot of the treatment beam precisely, before release of the pulse, as well as the envelope of that same beam. The latter characteristic enables the operator of the installation to make sure that the treatment beam will not, on passage, reach a zone different from the one to be treated. The marking beam is obtained on exit from the generator by means of a mechanism with rotating prisms that divide the laser radiation produced into two elementary beams, which will turn around the treatment beam so as to materialize its envelope. Detection of the fortuitous encounter of one of those elementary beams with an obstacle is further improved by a modulating device alternately interrupting either beam.

Finally, the optical head of the above-mentioned installation also contains a relatively complex system of optical elements like prisms, mirrors and lenses making it possible to focus the different illuminating, marking and treatment beams on the same spot of the eye, through a contact lens applied to the cornea. In order always to guarantee perfect focusing of those beams on a same spot, on which the observation device must also be focused, while allowing for a displacement of that focusing spot in the axis of the beams, it has proved useful to provide a single focusing lens at the exit of the optical head. Now, the need to bring parallel illuminating and treatment beams as well as the rotating marking beam on that single focusing lens and also to provide means for bringing the focal image into the observation device, has led to a complicated structure requiring numerous successive reflections for the different optical beams.

That is why this invention proposes a simplified optical head no longer necessarily containing an integrated illuminating device. This head embraces a limited number of optical elements, which results not only in a lower cost and a simpler assembly, but also in a better optical efficiency. The latter improvement makes it possible, notably, to reduce significantly the power of the treatment radiation used, and it also results in a greater brightness of the observation device. The advantage thus obtained of increased brightness amply compensates for elimination of the integrated illuminating device, which previously made it possible to focus the illuminating beam on the spot to be treated, avoiding parasitic reflections, but which appreciably complicated the design of the optical head. The new optical head can thus be used without difficulty with any independent illuminating system, of the slit lamp type, which is trained on the patient's eye.

According to one essential aspect of the invention, the optical head is equipped, above the focusing length, with a mirror that simultaneously assures the reflection of treatment and marking beams on that lens and transmission of the observation beam.

The marking and observation beams consisting of visible radiation, in contrast to the treatment beam, that mirror takes advantage of the localization of the marking beam forming the envelope of the treatment beam. For that purpose, it contains a center portion which assures passage of the observation beam and reflection of the treatment beam, and a ring-shaped portion that strikes the marking beam, and which is treated so as also to reflect it.

The invention will be clearly understood by reading the following description, giving in conjunction with the attached drawings, among which:

DETAILED DESCRIPTION

Figure 1:
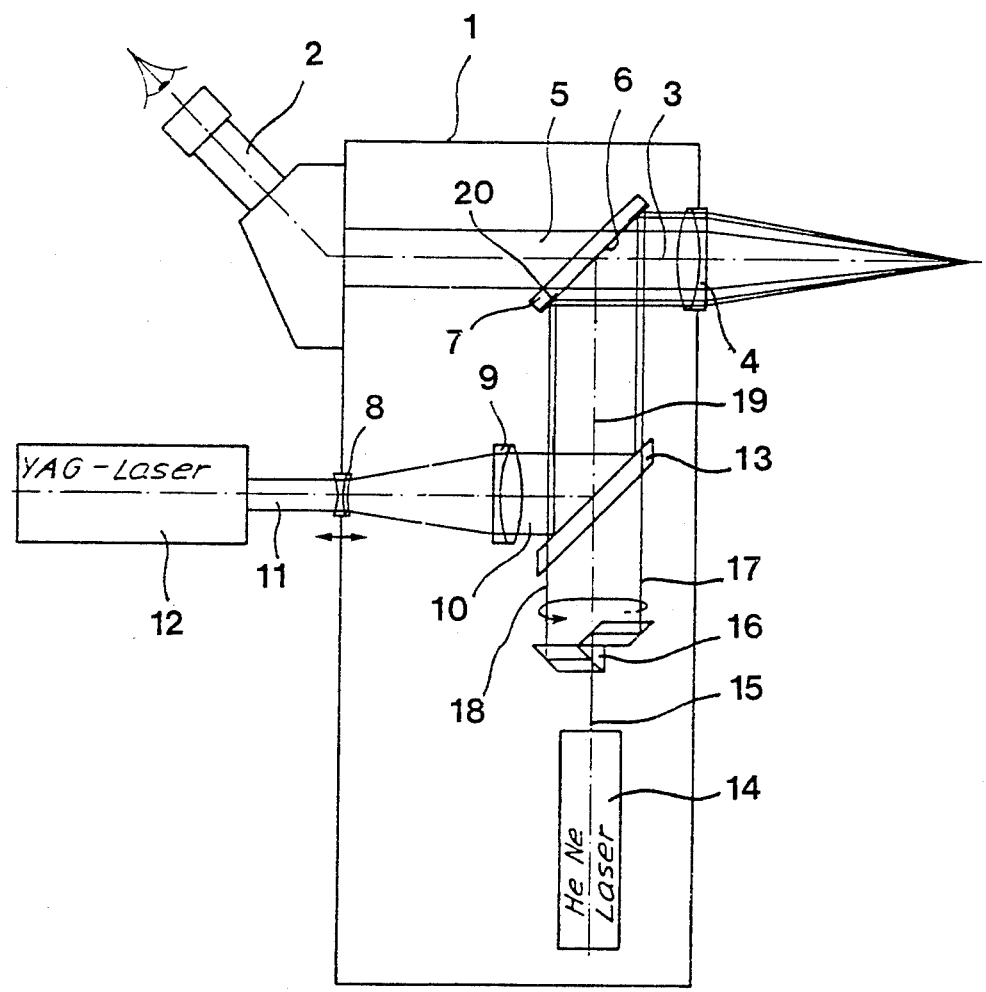
FIG. 1 is a schematic view of the optical head according to the invention.

As can best be seen on FIG. 1, the optical head 1 contains, notably, means of observation 2 on the optical axis 3 of which the focusing lens 4 is placed. The means of observation 2 can consist, for example, of a standard stereoscopic binocular assembly. The observation beam 5, which brings the image of focus F of the lens 4 to the means of observation 2, directly crosses the center portion 6 of a first mirror 7 placed in front of the lens 4. That center part is formed by a surface having a maximum transmission coefficient in the visible range.

Furthermore, the optical head 1 also contains a defocusing lens 8 adjustable in position and a converging lens 9 defining a treatment beam 10 from the coherent radiation 11 produced outside the head 1 by an Nd-YAG laser type generator 12, the working wavelength of which is in the order of 1.06 $\mu$m. The lenses 8 and 9 thus constitute a beam widener of coherent beam 11. A second mirror 13 having a maximum reflection coefficient for that wavelength then sends the treatment beam 10 to the center portion of the first mirror 7, the surface of which exhibits that same characteristic. The treatment beam 10 is thus directed to the focusing lens 4 coaxial to the observation beam 5.

Finally, the optical head further contains a laser generator 14, e.g., of the He-Ne type, emitting in the visible range a coherent radiation 15. A separation and rotation device 16 is associated with the generator 14 to form a marking beam consisting of two elementary parts or rays 17 and 18 turning on an axis 19 which coincides with that of the treatment beam 10 above the first mirror 7. The spacing of the rays 17 and 18 very slightly exceeds the diameter of the treatment beam 10, so as to delimit the outer envelope of the latter. On its exit from the separation and rotation device 16, the marking beam 17, 18 crosses the second mirror 13, which has a maximum transmission coefficient in the visible range, and strikes the first mirror 7. A ring-shaped portion 20 of the latter, surrounding its center portion 6, is designed to reflect the marking beam 17, 18 to the focusing lens 4. For this purpose, that ring-shaped portion bears a coating reflecting in the visible range or at least for the wavelength of the marking beam, e.g., with aluminum base, the inner diameter of which is greater than that of the observation beam, in order not to intercept it, and the outer diameter of which is greater than the spacing of the rays 17 and 18 of the marking beam.

The means of observation 2, the laser generators 12 and 14, the separation and rotation device 16 and the focusing lens 4, as well as the operation of the installation as a whole, have been explained in great detail in the aforementioned European patent application, and it is therefore unnecessary to repeat the description here.

Figure 2:
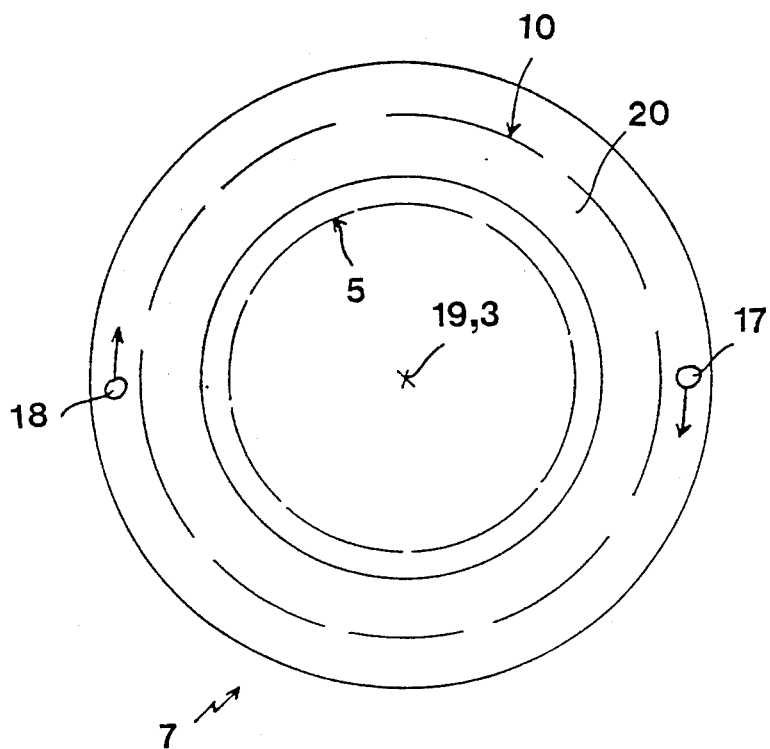
FIG. 2 is a view of the particular mirror used in the optical head of FIG. 1.

On FIG. 2, the first mirror 7 of the optical head has been represented, as well as the track of intersection of the observation beam 5, treatment beam 10 and marking beam 17 and 18, with its center portion 6 and its ring-shaped outer portion 20. That mirror is preferably a dichroic mirror, which has in its center position a maximum reflection coefficient for the wavelength of the Nd-YAG laser, in the order of 95% to 98%, for example, and a maximum transmission coefficient in the visible range, in the order of 80% of 90%, for example.

Although it has been described in relation to one of its particular embodiments, this invention is not at all limited to it, but, rather, lends itself to numerous modifications and variants, which will be evident to the expert.

What is claimed is:

1. The optical head of an installation for observation and treatment by a laser beam of an eye, comprising observing means for observing the zone of the eye to be treated, means for producing a treatment laser radiation beam, means for producing a marking laser radiation beam forming a visible envelope of the treatment beam, a focusing lens, the axis of which is coincident with the optical axis of the observing means for focusing the treatment and the marking beams on the zone of the eye to be treated, and a first mirror disposed on said treatment and marking beams between said observing means and said focusing lens for reflecting said treatment and marking beams towards said focusing lens, said first mirror having an outer portion intersecting only said marking beam, the reflection coefficient of said outer portion being maximum for the wavelength of said marking beam and an inner portion intersecting only said treatment beam, the reflection coefficient of said inner portion being maximum for the wavelength of said treatment beam and minimum for the wavelength of said marking beam, whereby said treatment beam is prevented from reaching said observing means after reflecting on the zone of the eye to be treated and said marking beam is able to reach said observing means after reflection on the zone of the eye to be treated.

2. An optical head according to claim 1, wherein the axial position of the diverging lens is adjustable.

3. The optical head of claim 1, wherein said inner portion has the shape of a circle centered on said optical axis of the observing means and said outer portion has the shape of a ring surrounding said circle.

4. The optical head of claim 1, wherein said means for producing a marking beam comprises a generator of a visible laser radiation beam coaxial with said treatment and marking beams and said means for producing a treatment beam comprises an entry lens for allowing an externally produced laser beam having the wavelength of said treatment beam to enter said optical head, further comprising a second mirror, the reflection coefficient of said second mirror being minimum for the wavelength of said visible beam and maximum for the wavelength of said externally produced laser beam, said second mirror being disposed on said visible laser beam and on said externally produced laser beam for forming said marking beam by transmission of said visible laser beam and said treatment beam by reflection of said externally produced laser beam.

5. The optical head of claim 3, wherein said means for producing a marking beam comprises a generator of a visible laser radiation beam coaxial with said treatment and marking beams and said means for producing a treatment beam comprises an entry lens for allowing an externally produced laser beam having the wavelength of said treatment beam to enter said optical head, further comprising a second mirror, the reflection coefficient of said second mirror being minimum for the wavelength of said visible beam and maximum for the wavelength of said externally produced laser beam, said second mirror being disposed on said visible laser beam and on said externally produced laser beam for forming said marking beam by transmission of said visible laser beam and said treatment beam by reflection of said externally produced laser beam.

6. The optical head of claim 4, wherein said entry lens is a diverging lens and said means for producing a treatment beam further comprises a converging lens disposed between said entry lens and said second mirror for producing, with said diverging lens, an enlargment of said externally produced beam.

7. The optical head of claim 5, wherein said entry lens is a diverging lens and said means for producing a treatment beam further comprises a converging lens disposed between said entry lens and said second mirror for producing, with said diverging lens, an enlargment of said externally produced beam.

8. The optical head of claim 4, wherein said means for producing a marking beam further comprises means for separating said visible laser beam into two separated beams symetrically disposed with respect to the axis of said treatment and marking beams and means for rotating said separated beams about said axis of the treatment and laser beams.

9. The optical head of claim 5, wherein said means for producing a marking beam further comprises means for separating said visible laser beam into two separated beams symetrically disposed with respect to the axis of said treatment and marking beams and means for rotating said separated beams about said axis of the treatment and laser beams.

* * * * *